(12) United States Patent
Becherer et al.

(10) Patent No.: US 8,921,588 B2
(45) Date of Patent: Dec. 30, 2014

(54) PROCESS FOR PREPARING SULFATES AND/OR SULFONATES IN A MICRO-REACTION SYSTEM

(75) Inventors: Miriam Becherer, Mülheim (DE); Bernhard Gutsche, Hilden (DE); Saskia Mueller-Meskamp, München (DE); Thomas Kruppa, Krefeld (DE); Kjeld Kraft, Dormagen (DE)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 14/241,705

(22) PCT Filed: Aug. 21, 2012

(86) PCT No.: PCT/EP2012/066231
§ 371 (c)(1),
(2), (4) Date: Jun. 2, 2014

(87) PCT Pub. No.: WO2013/030035
PCT Pub. Date: Mar. 7, 2013

(65) Prior Publication Data
US 2014/0303393 A1    Oct. 9, 2014

(30) Foreign Application Priority Data
Aug. 31, 2011  (EP) .................................. 11179488

(51) Int. Cl.
C07C 303/24    (2006.01)
C07C 303/06    (2006.01)
C07C 305/10    (2006.01)

(52) U.S. Cl.
CPC .................................... C07C 303/24 (2013.01)
USPC ........................................................... 558/33

(58) Field of Classification Search
USPC ........................................................... 558/33
See application file for complete search history.

(56) References Cited

U.S. PATENT DOCUMENTS 6,133,415 A    10/2000    Markley et al.

FOREIGN PATENT DOCUMENTS

| CN | 101607925 | 12/2009 |
|---|---|---|
| CN | 101947424 | 1/2011 |
| DE | 102008004044 | 7/2009 |
| EP | 0903174 | 3/1999 |

OTHER PUBLICATIONS

Angell, James B. et al., Silicon Micromechanical Devices, *Scientific American*, vol. 248 No. 4 1983, 44-55.
Burns, J.R. et al., Development of a Microreactor for Chemical Production, *Trans IChemE*, vol. 77 Part A May 1999, 206-211.
Gutsche, Bernhard et al., Thin-Film Reactors, *Ullmann's Encyclopedia of Industrial Chemistry*, vol. B4 2005, 10 pages.
Jahnisch, Klaus et al., Microprocessing Technology: Chemistry in Microstructure Reactors, *Angewandte Chemie*, vol. 116 2004, 86 pages.
Müller, A et al., Fluidic bus system for chemical process engineering in the laboratory and for small-scale production, *Chemical Engineering Journal*, vol. 17 2005, 205-214.

*Primary Examiner* — Kristin Vajda
(74) *Attorney, Agent, or Firm* — Servilla Whitney LLC

(57) ABSTRACT

Suggested is a process for preparing sulfates and/or sulfonates by adding sulfur trioxide to a compound comprising at least one hydroxyl function and/or at least one double bond, which is characterized in that
(i) the reaction is performed in a micro-reaction system (μ-reactor),
(ii) the sulfation/sulfonation agent used is a liquid sulfur trioxide, and
(iii) the reaction is conducted in the presence of 0 to 20 Vol.-% of air, inert gas or organic solvents.

15 Claims, No Drawings

PROCESS FOR PREPARING SULFATES AND/OR SULFONATES IN A MICRO-REACTION SYSTEM

CROSS-REFERENCE TO RELATED APPLICATIONS

This application is the national stage entry of PCT/EP2012/066231, filed on Aug. 21, 2012, which claims priority to European Patent application number 11179488.9, filed on Aug. 31, 2011, both of which are incorporated herein by reference in their entireties.

FIELD OF INVENTION

The present invention belongs to the area of anionic surfactants and refers to a specific sulfation/sulfonation process using liquid sulfur trioxide in a micro-reaction system.

STATE OF THE ART

The current technology for sulfation or sulfonation processes in order to produce anionic surfactants stars from gaseous sulfur dioxide which is oxidized to sulfur trioxide. Subsequently, the gaseous $SO_3$ is mixed with dry air and then reacted with organic compounds as for example primary alcohols, olefins, alkyl phenols, alkyl benzenes or their alkoxylation products. While the reaction with a hydroxyl group leads to a sulfate, addition of $SO_3$ to a double bond results in the formation of a sulfonate. The standard procedure is carried out in falling film reactors and described in detail for example by B. Gutsche et al. in Ullmann's Encyclopedia of Industrial Chemistry, Vol. B4, 1992. Companies like Ballestra or Chemithon provide commercial available reactors for the sulfation/sulfonation process using gaseous $SO_3$ diluted with air for decades. The dilution of the sulfur trioxide has been found mandatory in order to reduce oxidation power of the sulf(on)ation agent and avoid the formation of carbonaceous residues in the reactor. For example, in a very common embodiment, air is blown into a tube reactor forming a kind of curtain between the thin film of starting material and the $SO_3$.

During the last years, reactions in micro-systems have become interesting also for industrial purposes. One main reason is that in particular strong exothermic reaction can be much easier conducted in a micro than in a macro system. This is also true for sulfation/sulfonation. For example, Jähnisch et al. describe sulfation/sulfonation in a micronized falling film reactor [Chem. Eng. J. 107, 205-214 (2005)]. Kremer et al. teach the use of liquid sulfur trioxide diluted by air or inert gases in the sulfation/sulfonation of various starting materials [Chem. Spec. Mfr. Ass., Proc. Annu. Meet., 56, 105-109 (1970)]. The sulfation/sulfonation of organic starting materials, as e.g. naphthalene, using sulfur trioxide diluted by inert gases or organic solvents is object of Chinese patent applications CN 101947424 A and CN 101607925 A.

Although micro-reaction technology provides various advantages, in particular with regard to higher conversion, lower contents of waste materials and by-products, and significantly better product color, a major disadvantage is the need for diluting the liquid sulf(on)ation agent in high amounts of typical about 90 Vol.-%, since inert gases are extremely expensive and using air requires a high electric energy demand for compression and drying.

Therefore, the object of the present invention has been to provide a process for sulfation or sulfonation in a micro-reaction system using liquid sulfur trioxide as sulf(on)ation agent that is free from the disadvantages cited above and is particular useful for the manufacture of anionic surfactants with low level of unwanted by-products.

DESCRIPTION OF THE INVENTION

Object of the present invention is a process for preparing sulfates and/or sulfonates by adding sulfur trioxide to a compound comprising at least one hydroxyl function and/or at least one double bond, which is characterized in that
(i) the reaction is performed in a micro-reaction system (μ-reactor),
(ii) the sulfation/sulfonation agent used is a liquid sulfur trioxide, and
(iii) the reaction is conducted in the presence of 0 to 20 Vol.-% of air, inert gas or organic solvents.

Surprisingly, it has been observed that despite the prejudices mentioned in the state of the art it is possible to run the sulfation or sulfonation of organic materials by means of liquid sulfur trioxide in different types of micro-reaction systems simply either in the absence of air, inert gas or organic solvents or at low dilution rates of 1 to 20, preferably 5 to 10 Vol.-%. Obviously, this simple, but unexpected observation allows reducing the economic framework of such process significantly, since sulf(on)ation products are obtainable in high yields and high quality under simple process conditions.

Structured Reactors and Micro-Reaction Systems

A central element of the present invention consists in the finding that structured reactors enable the oxidation of ethylene and propylene to be performed irrespective of the explosion limits, since the reaction can be conducted isothermally, the reactants have only a minimal residence time in the reactor and the reaction channels have diameters which do not exceed the maximum experimental safe gap. The term "maximum experimental safe gap" is understood to mean the maximum diameter of a reactor at which a flame resulting from explosion is still automatically extinguished. These circumstances make it possible to use any mixtures of ethylene or propylene and oxidizing agent and nevertheless also to operate the reactor safely in the explosion range.

The term "structured reactor" is understood to mean an array of reaction channels which can be operated individually, in modules or else altogether and are disposed in a matrix which serves for stabilization, securing, heating or cooling. A preferred embodiment of a structured reactor is that of micro-reaction systems, which are also referred to in general as micro- or μ-reactors. They have the feature that at least one of the three dimensions of the reaction chamber has a measurement in the range from 1 to 2000 μm, and they thus feature a high transfer-specific inner surface area, short residence times of the reactants and high specific heat and mass transfer performances. A detailed article on this subject can be found, for example, in Jähnisch et al. in Angewandte Chemie Vol. 116, 410-451 (2004). Reference is made by way of example to European patent application EP 0903174 A1 (Bayer), in which the liquid phase oxidation of organic compounds in a micro-reactor consisting of an array of parallel reaction channels is described. Micro-reactors may additionally comprise microelectronic components as integral constituents. In contrast to known micro-analytical systems, it is by no means necessary in the micro-reactors that all lateral dimensions of the reaction chamber are within the μm range. Instead, their dimensions are determined exclusively by the type of reaction. Accordingly, for particular reactions, useful micro-reactors are also those in which a particular number of micro-channels are bundled, such that micro- and macro-channels or parallel operation of a multitude of micro-channels may be present alongside one another. The channels are preferably arranged parallel to one another in order to enable a high throughput and to keep the pressure drop as low as possible.

Supports

The micro-reaction systems can be made in one piece for example from ceramic or steel (Hastelloy) or are mounted on a support.

The supports in which the structure and dimensions of the micro-reaction systems are defined may be material combinations, for example silicon-silicon, glass-glass, metal-metal, metal-plastic, plastic-plastic or ceramic-ceramic, or combinations of these materials, although the preferred embodiment is a silicon-glass composite. Useful supports also include polyacrylates which are produced by layer-by-layer hardening and are particularly inexpensive to produce. A further alternative is that of HAT ceramics, specifically those which are surrounded by a pressure-resistant jacket, and also all-metal reactors in which the reaction channels are coated appropriately to prevent decomposition of the oxidizing agent. A wafer of thickness, for example, from 100 to 2000 µm, preferably about 400 µm, is structured preferably by means of suitable micro-structuring or etching techniques, for example reactive ion etching, through which it is possible, for example, to manufacture three-dimensional structures irrespective of the crystal orientation in silicon [cf. James et al. in Sci. Am. 4, 248 (1993)]. It is also possible, for example, to treat micro-reactors of glass in the same way.

Wafers treated in this way may have from 10 to 1000, preferably from 100 to 500 and especially from 200 to 300 micro-reaction systems running parallel to one another, which may be actuated and operated either in parallel or sequentially. The geometry, i.e. the two-dimensional profile of the channels, may be very different: possible profiles include straight lines, curves, angles and the like, and combinations of these shape elements. Not all micro-reaction systems need have the same geometry. The structures feature measurements of from about 1 to 2000 µm, preferably from about 50 to 1500 µm, more preferably from about 10 to 1000 µm, and vertical walls, the depth of the channels being from about 20 to 1800 µm and preferably from about 200 to 500 µm. The cross sections of each micro-reaction chamber, which may but need not be square, are generally in the order of magnitude of from about 20×20 to 1500×1500 µm$^2$ and especially from about 100×100 to 300×300 µm$^2$, as is specified as typical, for example, by Burns et al. in Trans IChemE 77(5), 206 (1999). Typically, the micro-reaction systems are channels which have a length of from about 1 to 5000 and preferably about 25 to 1000 mm.

To supply the micro-reaction chambers with the reactants, the wafer is etched through at the points intended for this purpose.

Finally, the structured wafer is bonded by a suitable process, for example anodic bonding, to a further wafer, for example of glass, preferably Pyrex glass, and the individual flow channels are sealed tightly to one another. Of course, depending on the substrate material, other construction and bonding techniques are also possible to realize impervious flow systems, which will be apparent to the person skilled in the art, without any need for an inventive step for this purpose.

Structuring of the Micro-Reactors

The micro-reaction systems may be divided into one or more mixing zones, one or more reaction zones, one or more mixing and reaction zones, one or more heating and cooling zones, or any combinations thereof. They preferably have three zones, specifically two reaction zones and one cooling zone, as a result of which especially two- or multistage reactions can be carried out efficiently in the liquid phase or else in the gaseous phase. In the first zone, two reaction participants are mixed and reacted; in the second zone, the reaction between the product of the first zone and a further reactant takes place, while the termination of the reaction is brought about in the third zone by lowering the temperature. It is not absolutely necessary to thermally strictly separate the first reaction zone and the second reaction zone from one another. Specifically, when the addition of a further reactant is required or several mixing points are desired instead of one, this can also take place in reaction zone 2 over and above zone 1. The micro-reaction systems may be operated sequentially or else simultaneously, i.e. in parallel with defined amounts of reactant in each case and having identical or different geometries. For example it is possible to start with small channels having a width of about 200 µm and enlarging them over the length of the reactor to a width of about 800 µm.

A further possible way in which the geometry of the micro-reaction systems may differ consists in the mixing angle at which the reactants meet one another and which may be between 15 and 270° and preferably from 45 to 180°. Furthermore, it is possible to cool or to heat each of the three zones independently, or to vary the temperature within one zone as desired, the reaction chambers in this example being channels whose length per zone may be from 10 to 500 mm.

Preferred Embodiments and Process Conditions

Basically, the structured micro reactors which were found suitable for conducting the reaction comprise at least one, preferably up to three mixing zones and at least one zone of reaction. Typically the mixer shows a channel width of about 10 to 2000 µm and the reactor of about 100 to 5000 µm.

In a preferred embodiment, the micro-reaction system is either a micro-multi-channel reactor with about 100 to about 1,000,000 and preferably about 500 to about 250,000 micro channels or a micro-tube bundle reactor with about 1 to 100, preferably about 40 to 80 and more preferably about 50 to 70 micro-tubes. It is also possible to conduct the process in a micro-falling film reactor. At least in one dimension of the reactor the channel width is between about 20 and 2000 µm.

The molar ratio $SO_3$ to organic compound can vary between about 0.5 to 3.0, preferably about 0.8 to 2.6:1, more preferably about 0.9 to 1.5:1 and most preferably about 1:1. It should be noted that the reaction with liquid sulfur trioxide for example in a micro multi-channel reactor allows using higher $SO_3$ concentrations compared to working in a macro reactor (e.g. a falling film reactor), without losing color performance of the reaction products. Since no or very little dilution is necessary the sulf(on)ation agent can be used directly without evaporation coming from the supplying facility (e.g. pipeline, bottle etc.). It is possible to perform the sulfation/sulfonation at temperatures in the range from about −20 to 180° C., however with respect to product color and yield it has been found rather advantageously to adjust the temperature to about 30 to 60° C. and avoid any increase caused by the exothermic reaction by external cooling. In the alternative also high temperatures of about 60 to 120° C. are possible on condition that the residence time is very short. The cooling of the reactor can take place by heat exchange in parallel, counter-current or cross-current flow.

Since micro-reaction systems allow a precise adjustment of residence time, a defined degree of reaction and significantly lower levels of unwanted sulfuric acid and—in case of polyglycol ethers as starting materials—dioxane can be achieved.

Also intensified mixing of the starting materials and SO$_3$ in the mixing area of the micro-reaction systems ensures high homogeneity of the mixtures and a precise stoichiometric reaction process.

Once the sulfation/sulfonation has taken place it is necessary to subject the acidic reaction products to a neutralization step. This can be done in a conventional neutralization equipment, however, it is by far preferred to conduct neutralization also in a micro-reaction system comprising one inlet for the crude sulf(on)ation product and another one for the neutralization gent, a mixing area and a heat transfer area. Suitable neutralization agents encompass alkaline hydroxide solutions as for example aqueous sodium or potassium hydroxide solutions, ammonia, alkyl amines or alkanol amines.

Due to defined stoichiometric ratios of the compounds, less excess of sulfur trioxide has to be destroyed. Also the mixtures contain less sulfur dioxide since no conversion from liquid sulfur to sulfur trioxide is necessary. Therefore, it has been observed that sulf(on)ation using a micro-reaction system and undiluted liquid sulfur trioxide requires less ageing, representing an additional advantage over the prior art in terms of time, energy and costs.

Starting Materials

As far as the starting materials are concerned the process is not critical. Basically, all educts which are available for introducing a sulfate or sulfonate group into the molecule represent suitable starting materials.

A first group of preferred educts encompass compounds comprising at least one hydroxyl moiety following general formula (I)

$$R^1(CO)_nO(AO)_mH \quad (I)$$

in which
R$^1$ stands for an saturated or unsaturated, optionally hydroxy substituted hydrocarbyl group having about 1 to 22, preferably about 12 to 18 carbon atoms and 0 or 1 to 3 double bonds, or an alkyl phenol group having about 1 to 12, preferably about 6 to 9 carbon atoms in the alkyl chain;
n stands either for 0 or 1;
m stands either for 0 or an integer of about 2 to 200, preferably about 1 to 50 and more preferably about 1 to 25; and
AO stands for an ethylene oxide, propylene oxide or butylene oxide unit or their mixtures.

This group encompasses in particular primary alcohols and the respective polyglycol ethers, as for example ethanol, propanol, isopropyl alcohol, butanol and its isomers, pentanol, hexanol, octanol, 2-ethylhexanol, decanol, lauryl alcohol, myrystyl alcohol, cetyl alcohol, stearyl alcohol, cetearyl alcohol, isostearyl alcohol, 12-hydroxy stearyl alcohol, oleyl alcohol, elaidyl alcohol, linolyl alcohol, linolenyl alcohol, conjugated linolyl alcohol, ricinoleyl alcohol, gadoleyl alcohol, arachidonyl alcohol, behenyl alcohol, erucyl alcohol, and their technical mixtures as for example coco fatty alcohol or tallow fatty alcohol. Suitable polyglycol ethers are adducts of on average about 1 to 100, preferably about 2 to 50 and more preferably about 5 to 25 moles ethylene oxide, propylene oxide and/or butylene oxide to said primary alcohols. In case mixtures of ethylene and propylene oxide are applied the resulting polyglycol ethers may show a block or random distribution of the different units. As far as ethoxylates are concerned these products may also show a so-called narrow range distribution. The process according to the present invention is particular useful for the manufacture of C$_{12}$-C$_{18}$ fatty alcohol ether sulfates with an average degree of ethoxylation of about 1 to 10, preferably about 2, since these products, representing major anionic surfactants for both detergent and cosmetics industry, show a significantly lower level of unwanted by-products, in particular dioxane, than similar products produced in standard multi-tube sulfation reactors.

A second group of suitable starting materials comprises alkoxylation products of carboxylic acids, such as capronic acid, caprylic acid, 2-ethylhexanoic acid, caprinic acid, lauric acid, myristic acid, palmitic acid, palmoleic acid, stearic acid, isostearic acid, oleic acid, elaidinic acid, linoic acid, linolenic acid, 12-hydroxy stearic acid, ricinoleic acid, gadoleic acid, arachidonic acid, behenic acid, erucic acid and their technical mixtures, like for example coco fatty acid, palm fatty acid, tallow fatty acid, sunflower fatty acid, soy fatty acid and the like. Suitable polyglycol ethers are adducts of on average about 1 to 100, preferably about 2 to 50 and more preferably 5 to 25 moles ethylene oxide, propylene oxide and/or butylene oxide to said carboxylic acids. In case mixtures of ethylene and propylene oxide are applied the resulting polyglycol ethers may show a block or random distribution of the different units.

Also suitable are alkoxylation products of alkyl phenols comprising about 1 to 12 and preferably about 6 to 9 carbon atoms in the alkyl chain, such as hexyl phenol, heptyl phenol, octyl phenol, nonyl phenol or their mixtures. Again, suitable polyglycol ethers are adducts of on average about 1 to 200, preferably about 1 to 50 and more preferably about 1 to 25 moles ethylene oxide, propylene oxide and/or butylene oxide to said alkyl phenols. In case mixtures of ethylene and propylene oxide are applied the resulting polyglycol ethers may show a block or random distribution of the different units.

A second group of suitable starting materials encompasses compounds comprising at least one double bond follow general formula (II)

$$R^2\text{-Ph} \quad (II)$$

in which R$^2$ stands for an alkyl group having about 1 to 22 carbon atoms and Ph represents a phenyl group. This group mainly concerns alkyl benzenes, where a sulfonate group is introduced into the aromatic ring structure. It has to be understood that of course also alkyl phenols can react in the same way, that means that sulfonation of the aromatic ring structure takes place beside sulfation of the hydroxyl moiety. Since sulfation represents the by far faster reaction, adding sulfur trioxide for example to a nonyl phenol+10EO molecule mainly leads to the formation of the respective sulfate, while the sulfonate is formed in minor amounts.

Also suitable starting materials for the formation of sulfonates are olefins and functionalized olefins, like for example unsaturated primary alcohols, unsaturated mono- or dicarboxylic acids and their esters, unsaturated synthetic glycerides or natural occurring fats and oils, unsaturated amides and their mixtures. Typically these compounds show a chain length of C$_6$ to C$_{22}$.

EXAMPLES

Example 1

Synthesis of Nonyl Phenol+25EO Sulfate, Sodium Salt

For the experiments, a micro-reaction system consisting of a 400 μm-thick silicon wafer was used, which was joined to a Pyrex glass wafer. 20 parallel, linear channels, with a depth of 300 μm and a cross section of the micro-reaction chambers of 300×300 μm$^2$ had been etched into the silicon wafer. The channels were operated in parallel and were each etched through for reactant introduction and for product removal. 481 g (0.38 mol) Nonylphenol+25EO were reacted with 30.2 g (0.38 mol) liquid sulfur trioxide at 35 to 40° C. Neutralization was performed with 30.2 g of 50% b.w. aqueous sodium hydroxide solution at 80° C. The neutralization product was aged for another 20 min.

Example 2

Synthesis of Lauryl Alcohol+2EO Sulfate, Sodium Salt

A micro-multi-channel reactor consisting of about 500 channels with a channel width and a channel depth of about 300 μm and a channel length of about 50 mm were used for conducting the sulfation of a lauryl alcohol+2EO (Dehydrol® LS2, BASF Personal Care & Nutrition GmbH, Dusseldorf). The channels were operated in parallel and were etched through for educt input and product removal. The cooling channels corresponded in their diameter to the reaction channels. By virtue of the construction of the microreactor, contact between liquid sulfur trioxide and the fatty alcohol polyglycol ether took place solely in the cooled region. The reaction was carried out in countercurrent, although co-current operation is also possible. The reaction was conducted at an equimolar ratio of $SO_3$ and polyglycol ether and a temperature of 35° C. Neutralization was performed with 50% b.w. aqueous sodium hydroxide solution at 80° C. in a micro-mixing unit attached to the micro-multi-channel reactor. The neutralization product was aged for another 20 min. The resulting lauryl alcohol+2EO sulfate sodium salt was obtained as a clear, colorless liquid that was substantially free of dioxane.

The invention claimed is:

1. A process for preparing sulfates and/or sulfonates by adding sulfur trioxide to a compound comprising at least one hydroxyl function and/or at least one double bond, characterized in that:
    (i) the reaction is performed in a micro-reaction system,
    (ii) the sulfation/sulfonation agent comprises a liquid sulfur trioxide, and
    (iii) the reaction is conducted in the presence of 0 to 20 vol.-% of air, inert gas, or organic solvents.
2. The process of claim 1, wherein the micro-reaction system is made from ceramic or steel, and is optionally mounted on a support.
3. The process of claim 1, wherein the micro-reaction system has at least one inlet for the reactants and at least one outlet for the products.
4. The process of claim 1, wherein the support is a silicon-glass composite.
5. The process of claim 1, comprising a plurality of micro-reaction systems all have the same geometry or different geometries.
6. The process of claim 5, wherein the micro-reaction systems have dimensions in the range from 1 to 2000 μm in at least one dimension.
7. The process of claim 5, wherein the micro-reaction systems are channels which have a length of from 1 to 5000 mm.
8. The process of claim 5, wherein the micro-reaction systems have one or more mixing zones, one or more reaction zones, one or more mixing and reaction zones, one or more heating or cooling zones, or any combinations thereof.
9. The process of claim 1, wherein the micro-reaction system is a micro-multi-channel reactor with 50 to 1,000,000 micro-channels.
10. The process of claim 1, wherein the micro-reaction system is a micro-tube bundle reactor with 1 to 100 micro-tubes.
11. The process of claim 1, wherein the sulfation/sulfonation is performed at temperatures in the range from −20 to 180° C.
12. The process of claim 1, further comprising neutralizing the sulfation/sulfonation products.
13. The process of claim 1, wherein the compounds comprising at least one hydroxyl moiety follow general formula (I)

$$R^1(CO)_nO(AO)_mH \qquad (I)$$

in which
    $R^1$ stands for an saturated or unsaturated, optionally hydroxy substituted hydrocarbyl group having 1 to 22 carbon atoms and 0 or 1 to 3 double bonds, or an alkyl phenol group having 1 to 12 carbon atoms in the alkyl chain;
    n stands either for 0 or 1;
    m stands either for 0 or an integer of 1 to 200; and
    AO stands for an ethylene oxide, propylene oxide or butylene oxide unit or their mixtures.
14. The process of claim 1, wherein the compounds comprising at least one double bond follow general formula (II)

$$R^2\text{-Ph} \qquad (II)$$

in which $R^2$ stands for an alkyl group having 1 to 22 carbon atoms and Ph represents a phenyl group.
15. The process of claim 14, wherein the compounds comprising at least one double bond are selected from the group consisting of olefins, unsaturated primary alcohols, unsaturated mono- or dicarboxylic acids and their esters, unsaturated synthetic glycerides or natural occurring fats and oils, unsaturated amides and their mixtures.

* * * * *